(12) United States Patent
Walker

(10) Patent No.: US 11,980,375 B2
(45) Date of Patent: May 14, 2024

(54) ANTERIOR CRUCIATE LIGAMENT RECONSTRUCTION

(71) Applicant: PMSW RESEARCH PTY LTD, Bellevue Hill (AU)

(72) Inventor: Peter Walker, Bellevue Hill (AU)

( * ) Notice: Subject to any disclaimer, the term of this patent is extended or adjusted under 35 U.S.C. 154(b) by 940 days.

(21) Appl. No.: 16/970,766

(22) PCT Filed: Feb. 14, 2019

(86) PCT No.: PCT/AU2019/050113
§ 371 (c)(1),
(2) Date: Aug. 18, 2020

(87) PCT Pub. No.: WO2019/161436
PCT Pub. Date: Aug. 29, 2019

(65) Prior Publication Data
US 2020/0375615 A1    Dec. 3, 2020

(30) Foreign Application Priority Data
Feb. 22, 2018 (AU) ................................ 2018900570

(51) Int. Cl.
*A61B 17/17* (2006.01)
*A61B 17/16* (2006.01)
*A61F 2/08* (2006.01)

(52) U.S. Cl.
CPC ...... *A61B 17/1714* (2013.01); *A61B 17/1675* (2013.01); *A61B 17/1764* (2013.01);
(Continued)

(58) Field of Classification Search
CPC ............ A61B 17/1714; A61B 17/1675; A61B 17/1764; A61B 17/1796; A61F 2/0811; A61F 2002/0882
(Continued)

(56) References Cited

U.S. PATENT DOCUMENTS 5,797,918 A * 8/1998 McGuire ............ A61B 17/1714
606/104
5,908,423 A * 6/1999 Kashuba .............. A61B 17/175
408/127

(Continued)

FOREIGN PATENT DOCUMENTS

WO    2017122215 A1    7/2017

OTHER PUBLICATIONS

International Search Report dated May 8, 2019 from PCT Application No. PCT/AU2019/050113.

*Primary Examiner* — Jessica Weiss
(74) *Attorney, Agent, or Firm* — INNOVATION CAPITAL LAW GROUP, LLP; Vic Lin

(57) ABSTRACT

There is provided herein and improved anterior cruciate ligament reconstruction technique which comprises drilling a guide wire straight through a tibial passage and then at an angle from an ACL insertion point straight through a femoral passage. A reamer is then attached to a proximal end of the guidewire. The reamer has a distal cutting head, a distal flexible shaft, a proximal cutting head and a proximal flexible shaft. The proximal cutting head has a greater diameter than that of the distal cutting head. The reamer is drilled to follow the guidewire until the distal cutting head passes through the femoral cortex. The reamer is then retrieved at a proximal end thereof, thereby having created a larger diameter medial passage portion and a smaller diameter lateral passage portion within the femoral passage in a single pass, thereafter being ready for insertion of a graft, including by endobutton fixation.

25 Claims, 11 Drawing Sheets

(52) U.S. Cl.
CPC ........ *A61B 17/1796* (2013.01); *A61F 2/0811* (2013.01); *A61F 2002/0882* (2013.01)

(58) Field of Classification Search
USPC .......................................................... 606/80
See application file for complete search history.

(56) References Cited

U.S. PATENT DOCUMENTS

| | | | |
|---|---|---|---|
| 2003/0187449 A1* | 10/2003 | McCleary | A61B 17/1668 606/80 |
| 2003/0220644 A1 | 11/2003 | Thelen et al. | |
| 2006/0106393 A1* | 5/2006 | Huebner | A61B 17/164 606/80 |
| 2007/0093840 A1* | 4/2007 | Pacelli | A61B 17/1631 606/80 |
| 2007/0250067 A1* | 10/2007 | Schmieding | A61B 17/1764 606/96 |
| 2008/0140078 A1* | 6/2008 | Nelson | A61B 17/1642 606/80 |
| 2014/0276844 A1* | 9/2014 | Bourque | A61B 17/1631 606/80 |
| 2015/0066040 A1* | 3/2015 | Harbison | A61B 17/1714 606/96 |
| 2015/0127012 A1* | 5/2015 | Pilgeram | A61B 17/1637 606/88 |

\* cited by examiner

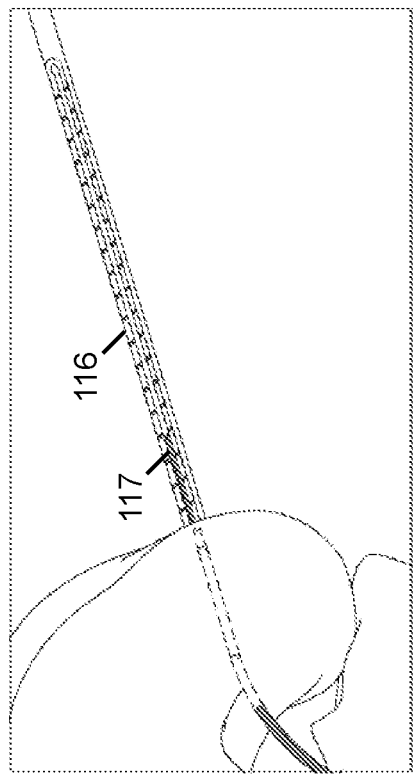
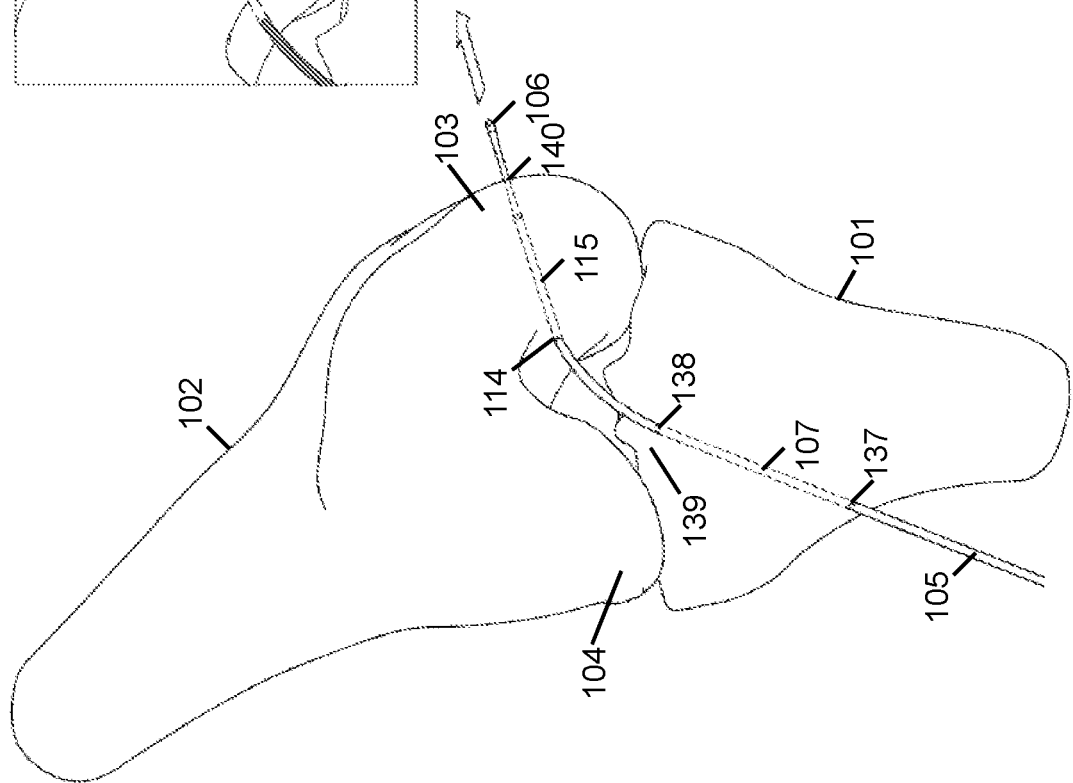
Figure 3B
Figure 3A

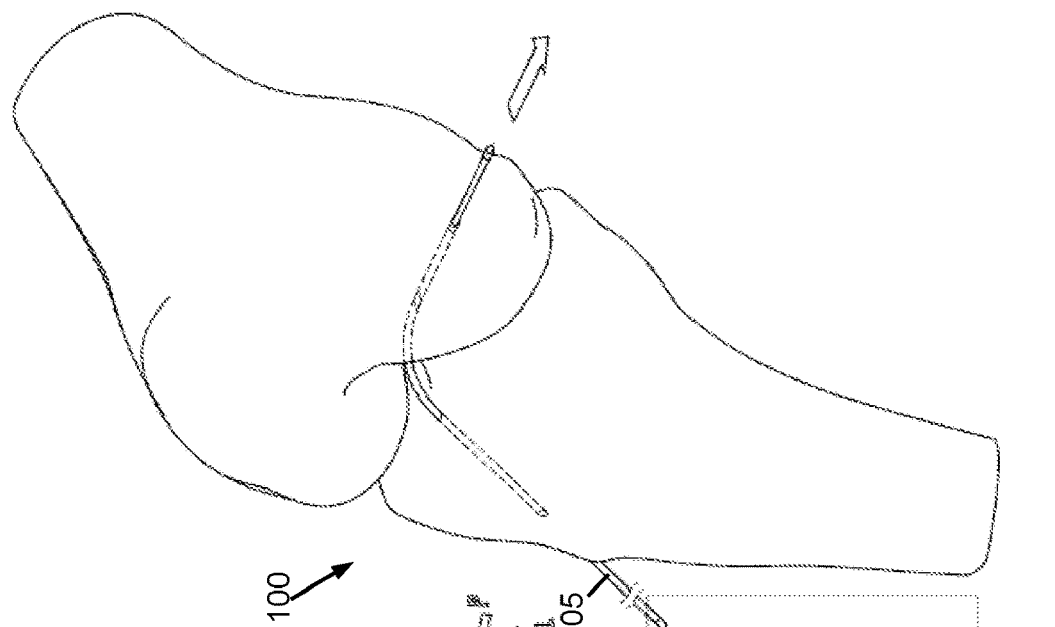
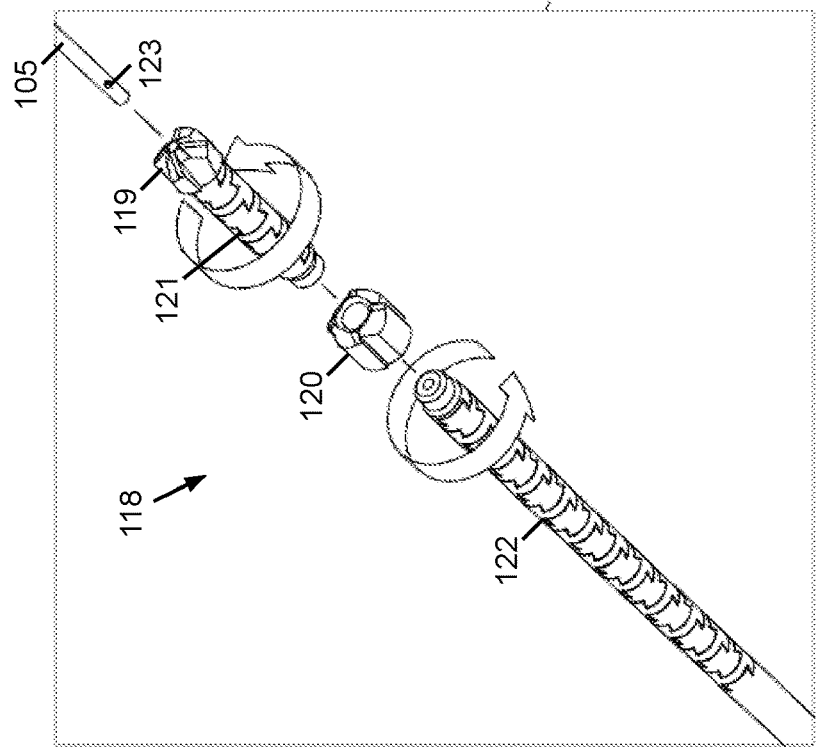

CANNULATED

UN-CANNULATED

ANTERIOR CRUCIATE LIGAMENT RECONSTRUCTION

FIELD OF THE INVENTION

The present invention relates to improvements in anterior cruciate ligament reconstruction.

BACKGROUND OF THE INVENTION

A ligament is fibrous tissue which connects two bones and which is frequently detached, torn, ruptured and the like as a result of injury or accident. One such ligament which is frequently damaged is the anterior cruciate ligament (ACL) which extends between the tibia and femur. A damaged ACL can cause instability of the knee joint and cause substantial pain and/or arthritis. It is estimated that over 100,000 ACL reconstructions are performed annually in the US alone.

A typical ACL reconstruction approach is the transtibial procedure wherein a guide is used to drill a tibial passage for the insertion of an offset guide therethrough. A guide wire is then inserted through the inserted offset guide for positioning towards the femur.

However, it is difficult to position the guide wire at the appropriately native ACL insertion point on the femur because the ACL insertion point is out of alignment with a tibial tunnel drilled for the guide wire and, as such, the transtibial technique may result in malpositioning leading to rotational instability.

To better position the ACL insertion point, a second type of common ACL technique is the anteromedial portal technique in which an offset guide is placed through a medial portal skin incision and into the joint to guide the guide wire. In accordance with this approach, the offset guide is not restrained by the tibial passage and therefore has more freedom to be placed anywhere along the femoral notch. However, there are several known difficulties with this technique including that hyperflexion of the knee is required for the anterior medial portal technique which is undesirous because the surgeon may lose visual reference to various anatomical landmarks visible at normal 90° flexion. Furthermore, hyperflexion is difficult when using a leg holder and may be impossible due to a patient's anatomy. Furthermore, there is a tendency for shorter tunnel lengths to be formed with this technique, resulting in the reduced tendon ingrowth distance of the femoral passage and therefore the fixation strength of the repair being compromised. The angle of the reaming also risks damaging the articular cartilage or lining of the medial femoral condyle.

Once the tibial and femoral passages have been formed by whichever technique, an autograft, allograft or artificial graft is pulled through these passages and fixed in place.

A common ACL are fixation technique is the endobutton fixation technique requiring a femoral passage having a lateral section of approximately 4.5 mm in diameter and a relatively larger medial section of approximately 6-10 mm in diameter.

Formations of these differing diameter sections of the femoral passage typically entails firstly inserting a smaller diameter cannulated reamer to follow coaxially over the guide wire to form the smaller diameter lateral section. The smaller diameter cannulated reamer is then removed whereafter a larger diameter cannulated reamer is inserted to again similarly go over the guide wire to form the larger diameter medial section.

For example, a technique by Versitomic (Stryker™) and Clancy (Smith and Nephew™) drills two flexible drills of different diameters in two passes using the medial portal technique. These drills are cannulated and follow the guide wire. However, these flexible drills suffer from problems of breakage and metallosis inducing friction when drilled over the guide wire. Furthermore, guide wires for this technique are required to be very flexible which only exacerbates these issues. A yet further issue with flexible guide wires is that, as these guide wires contact the lateral cortex of the femur at an angle of approximately 45°, these guide wires often skive off course the hard cortical bone.

A yet further issue with cannulated drills is that, if there is a requirement to change direction, the stiffness of the guidewire in addition to the stiffness of the drill makes such a manoeuvre difficult. Without an internal guidewire the mechanics of a flexible drill are constant.

Furthermore, this technique requires two distinct drilling passes of insertion and removal and drill sizes.

The present invention seeks to provide anterior cruciate ligament reconstruction procedures and instrumentation therefor, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

We found that existing techniques, including the endobutton fixation technique, have several disadvantages.

For example, the aforedescribed two pass prior art reaming procedure for the formation of dual diameter femoral passages is time-consuming, including in requiring detachment and replacement of reaming components.

Furthermore, when drilling the larger medial passage, the larger diameter reamer follows the relatively small diameter guidewire (such as having a diameter of approximately 2.4 mm mm) As the guidewire is unrestrained by the relatively larger already-formed passage (such as having a diameter of approximately 4.5 mm), we found that rotational eccentricity may cause the larger diameter reamer may deviate non-coaxially, thereby malforming the passage into being non-circular As such, there is provided herein and improved anterior cruciate ligament reconstruction technique which comprises drilling a guide wire to form a straight tibial passage through the tibia between an inferior anteromedial entrance and a tibial plateau exit of the tibia.

When the tip of the guidewire extends from the tibial plateau exit, the tip is bent towards the femoral condyle to direct the tip towards the anatomic ACL insertion point of the lateral femoral condyle.

The guidewire is drilled further to further form a straight femoral passage through the lateral femoral condyle between the ACL insertion point and a superior posterior lateral exit such that the tip of the guidewire extends from the femoral cortex. Furthermore, the straight femoral passage is at an angle with respect to the straight tibial passage.

A reamer is then attached to a proximal end of the guidewire. The reamer has a distal cutting head, a distal flexible shaft, a proximal cutting head and a proximal flexible shaft. The proximal cutting head has a greater diameter than that of the distal cutting head.

The reamer is drilled to follow the guidewire such that the reamer follows the guidewire straight through the tibial passage, bends between the tibial plateau exit and the ACL insertion point and follows straight through the femoral passage.

The reamer is drilled until such time that the distal cutting head passes through the femoral cortex at the superior posterior lateral exit and the proximal cutting head locates between the ACL insertion point and the superior posterolateral exit.

The reamer is then pulled at a proximal end thereof from the knee joint, thereby having enlarged the tibial passage to the diameter of the proximal cutting head and having enlarged the femoral passage to comprise a medial passage portion having a diameter of the proximal cutting head and a lateral passage portion having a diameter of the distal cutting head in a single pass.

As such, the present technique avoids problems of prior art of having to remove and replace components for the formation of the dual diameter femoral passages.

A distinct advantage of the present technique is that the knee does not have to be hyperflexed to gain the correct ACL entry point into the femur. The knee can simply be rested over the side of the bed requiring no help from an assistant.

Furthermore, the proximal cutting head follows directly behind the distal flexible shaft at the same time and is thereby constrained by the passage formed thereby, avoiding prior art coaxial misalignment problems.

Furthermore, as most orthopaedic instrument sets have multiple drills from 6 mm to 12 mm in 0.5 mm increments to drill the medial tunnel. The present technique allows the proximal cutting head and a proximal flexible shaft for the formation of the larger medial passage to be disposable, thereby significantly reducing inventory.

Whereas flexible reamers exist, including as is disclosed in US 2007/0093840 A1 (PACELLI et al.) 26 Apr. 2007 [hereinafter referred to as D1], including dual diameter reamers, such as is disclosed in US 2003/0220644 A1 (THELAN et al.) 27 Nov. 2003 [hereinafter referred to as D2], dual diameter flexible reamers have hitherto not been used, or suggested for use, specifically for ACL reconstruction, especially those involving endobutton fixation.

Indeed, to the contrary, the current state of "single pass" dual diameter reaming of the femoral passage is indicated by US 2014/0276844 A1 (SMITH & NEPHEW, INC.) 18 Sep. 2014 [hereinafter referred to as D3] which used a drill which is drilled laterally into the lateral femoral condyle. The drill has a cutting member which flicks outwardly to then form the relatively larger passage when the drill is pulled back. The cutting members then retracted again to remove the drill, thereby having formed the dual diameter femoral passages.

Furthermore, we found that it is often difficult to gauge the insertion depth of the relatively larger reamer which may lead to formation of passages of improper length. However, as the length of the present distal flexible shaft is known, the exact location of the proximal cutting head may be gauged within the lateral femoral condyle by the extent of the distal flexible shaft from the femoral condyle.

Furthermore, when using prior art cannulated reamers, if there is any angle change of the guide wire relative to the reamer (which does occur particularly if the knee is moved after insertion of the guidewire), the guide wire can be broken inside the bone making retrieval difficult. Furthermore any change in direction between the guide wire and reamer can cause damage to the guide wire resulting in metallosis which if left inside the knee can cause irreversible damage.

An advantage of the present technique however is that if the drill breaks, portions may remain attached proximally or distally for separate retrieval. Similarly, if the guide wire where to break, portions thereof yet remain attached proximally or distally for ease of retrieval.

As such, in a preferred embodiment, the distal cutting head is configured to engage the guidewire coaxially such that, during reaming, the guidewire and the reamer move together in alignment along and elongate axis of the reamer.

As such, with such a configuration, the guidewire may be pulled to aid the reamer through the knee joint. Furthermore, this configuration may reduce or eliminate metallosis as compared to a cannulated variant. Furthermore, this configuration may allow the retrieval of the reamer if broken during use as a distal end thereof remains connected to the guidewire. Furthermore, the guide wire cannot be reamed through because the guide wire is pushed from the bone as the reamer enters.

In further embodiments, the distal cutting head may be configured to engage the guidewire coaxially such that the distal cutting head and the guidewire rotate together, thereby further reducing or eliminating metallosis and/or enhancing the mechanical connection between the guidewire and the distal cutting head. In embodiments, the distal cutting head may comprise a central threaded port for engaging corresponding threading of a proximal end of the guidewire. Furthermore, the threading may be relatively orientated such that the threading tightens when the reamer rotates, thereby avoiding unscrewing during operation. Other connections are envisaged within the purposive scope of the embodiments provided herein.

According to one aspect, there is provided anterior cruciate ligament reconstruction for a knee joint comprising a tibia and a femur, the reconstruction comprising: drilling a guide wire to form a straight tibial passage through the tibia between an inferior anteromedial entrance and a tibial plateau exit of the tibia; bending a tip of the guide wire extending from a tibial plateau exit towards an ACL insertion point at a lateral condyle of the femur; further drilling the guide wire to further form a straight femoral passage through the lateral condyle between the ACL insertion point and a superior posterolateral exit such that the tip extends from the femur and the femoral passage being angled with respect to the tibial passage; attaching a reamer to a proximal end of the guidewire, the reamer comprising a distal cutting head, a distal flexible shaft, a proximal cutting head and a proximal flexible shaft and wherein the proximal cutting head has a greater cutting diameter than that of the distal cutting head; drilling the reamer to follow the guidewire such that the reamer follows the guidewire straight through the tibial passage, bends between the tibial plateau exit and the ACL insertion point, and follows straight through the femoral passage until the distal cutting head passes through the superior posterolateral exit and the proximal cutting head locates between the ACL insertion point and the superior posterolateral exit; pulling the proximal end of the reamer to pull the reamer from the knee joint, thereby having enlarged the tibial passage to the diameter of the proximal cutting head and having enlarged the femoral passage to comprise a medial passage portion having the diameter of the proximal cutting head and a lateral passage portion having a diameter of the distal cutting head; and inserting and securing an anterior cruciate ligament replacement within the tibial passage and the femoral passage.

A proximal end of the guide wire may be connected to the distal cutting head such that the guide wire and the proximal cutting head move in alignment together along an elongate axis of the reamer during reaming.

The method may further comprise pulling the distal end of the guidewire during reaming to pull the reamer through the knee joint.

The proximal end of the guide wire may be connected to the distal side of the distal cutting head such that the guide wire and the proximal cutting head rotate together.

The proximal end of the guidewire may comprise threading which screws into threading of a central port of the distal cutting head.

The threading may be respectively orientated to tighten when the reamer rotates during reaming.

The distal cutting head may define a distal cutting face and wherein the distal cutting face may be rearwardly swept.

The distal cutting face may be angled to make a frustoconical cut.

The method may further comprise referencing the insertion depth of the proximal cutting head by referencing the length of the distal flexible shaft or guide wire extending from the superior posterolateral exit.

The method may further comprise using an elongate reference guide having depth reference markings thereon by placing the elongate reference guide against the lateral condyle the superior posterolateral exit and reading the location of the distal flexible shaft or guide wire with reference to the depth reference markings.

The method may comprise interchanging the proximal cutting head with one of a specific diameter according to patient specific anatomy dependant on the size of the graft to be used.

The reamer may be a modular reamer of modular construction such that at least the proximal cutting head may be separable.

The modular reamer has the distal cutting head and the distal flexible shaft being inseparable.

A proximal end of the distal flexible shaft may comprise threading which screws into threading of a central port of the proximal cutting head. Other methods of attachment may be employed also.

The threading may be respectively orientated to tighten when the reamer rotates during reaming.

The reconstruction may further comprise inserting bending guide between the femoral condyles to bend the tip of the guidewire towards the ACL insertion point.

The bending guide may comprise a rod and a guide wire engagement transversely orientated at a distal end thereof.

The guide wire engagement may define a transverse open channel which engages the guidewire there along.

The transverse open channel may be curved.

The rod may be cylindrical and wherein the bending guide may further comprise an inner rod which references a point of the joint and wherein the method may further comprise positioning the anteroposterior location of the tip of the guidewire by gauging the offset of the rod and the inner rod.

Inner rod has depth gauge markings thereon.

Inserting the bending guide may comprise inserting the bending guide through an incision.

The distal cutting head may comprise a diameter of less than 7 mm.

The distal cutting head may comprise a diameter of less than 6 mm.

The proximal cutting head may comprise a diameter of greater than 6 mm.

According to another aspect, there is provided a reamer comprising a distal cutting head, a distal flexible shaft, a proximal cutting head and a proximal flexible shaft and wherein the distal cutting head is configured to engage a guidewire coaxially such that, during reaming, the guidewire and the reamer move together in alignment along and elongate axis of the reamer.

The proximal cutting head may be further configured to engage the guidewire such that the guidewire and the reamer rotate together during reaming.

The proximal end of the guidewire may comprise threading which screws into threading of a central port of the distal cutting head.

The threading may be respectively orientated to tighten when the reamer rotates during reaming.

According to another aspect, there is provided a custom guide which may be modelled to fit the anatomy of the individual patient. The custom guide may comprise: an anteromedially aspect tibial referencing reamer guide; and a femoral intercondylar notch referencing femoral guidewire guide offset at an angle from the reamer guide.

The reamer guide may comprise an expansion plate which references the anteromedial aspect of the tibia.

A distal end of the tibial referencing reamer guide may comprise a step for seating the femoral intercondylar notch therein.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which:

FIG. 3 illustrates the guidewire having been inserted through both tibial and femoral passages and the utilisation of a depth gauge in accordance with an embodiment;

FIG. 4 illustrates the connecting together of a modular reamer to the proximal end of the guide wire in accordance with an embodiment;

DESCRIPTION OF EMBODIMENTS

Figure 1:
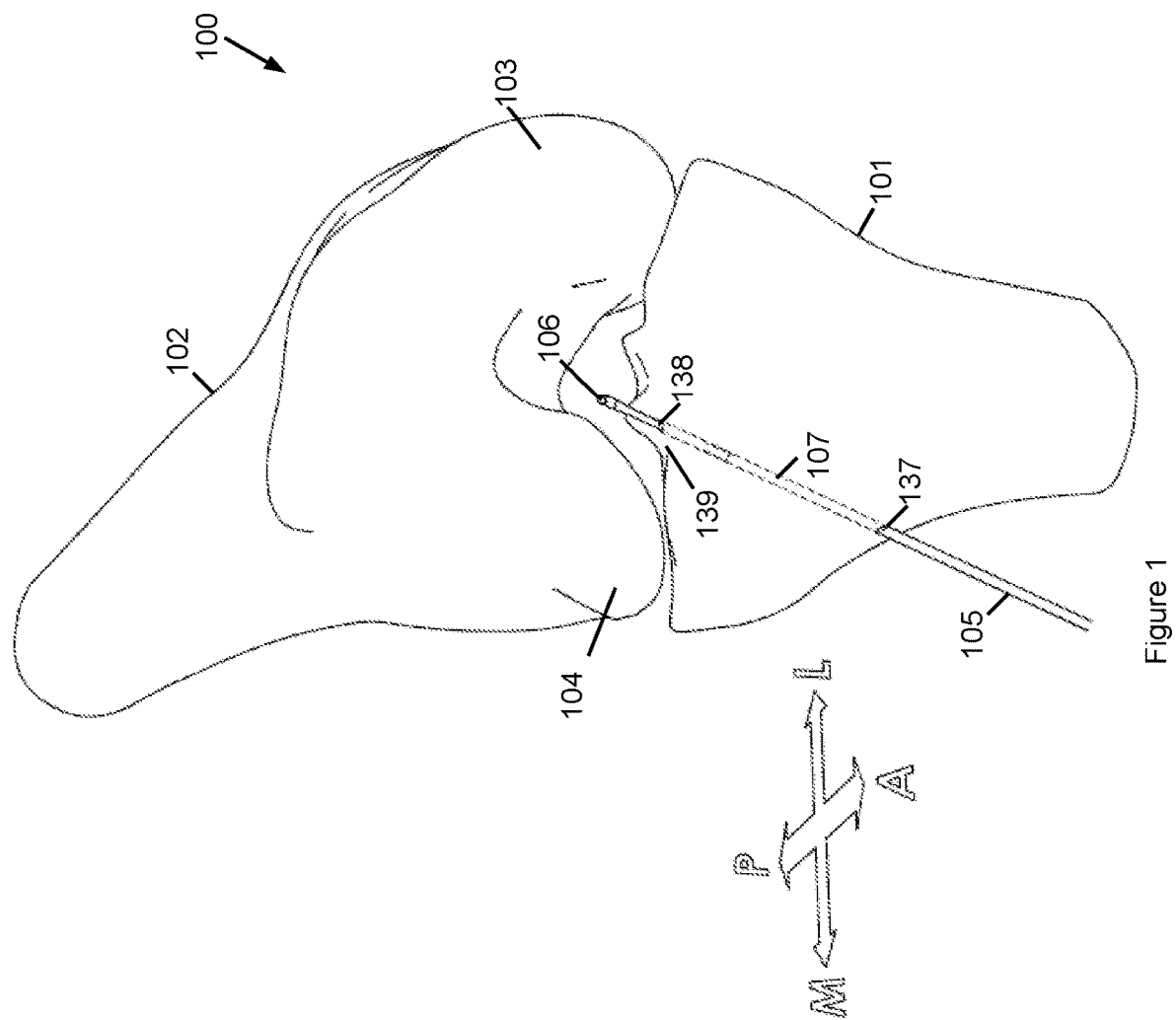
FIG. 1 illustrates a knee joint and the insertion of a guide wire through the tibia into the knee joint.

FIG. 1 shows a knee joint 100 comprising tibia 101 and a femur 102.

For illustrative convenience, the embodiments described herein will be described with reference to the orientational axes provided in FIG. 1 referencing the anterior (front), posterior (back), lateral (outside) and medial (inside) axes provided. Furthermore, the term proximal and derivatives thereof generally mean the closest end (including of the reamer described herein) and distal and derivatives thereof generally mean the furthest end or terminating point of an elongate device.

As such, the femur 102 comprises a lateral condyle 103 and a medial condyle 104 and the instrumentation and techniques provided herein are configured for forming passages through the tibia 101 and lateral condyle 103 of the femur 102 for ACL reconstruction.

FIG. 1 illustrates the drilling of a guide wire 105 to form a straight tibial passage 107 through the tibia 101 from an inferior anteromedial entrance 137 and out through a tibial plateau exit 138 of a tibial plateau 139 of the tibia 101.

The tip 106 of the guidewire may comprise a rotational cutting head to facilitate drilling through the bone.

Figure 2B:
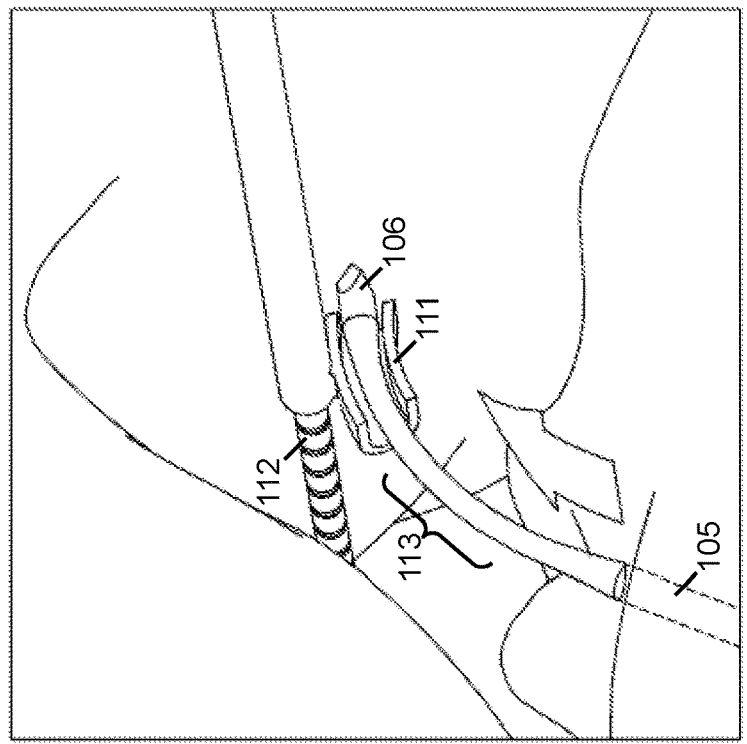
FIG. 2 illustrates the bending of the guidewire within the knee joint towards an ACL insertion point of the lateral femoral condyle using a depth positioning guide in accordance with an embodiment.
Figure 2A:
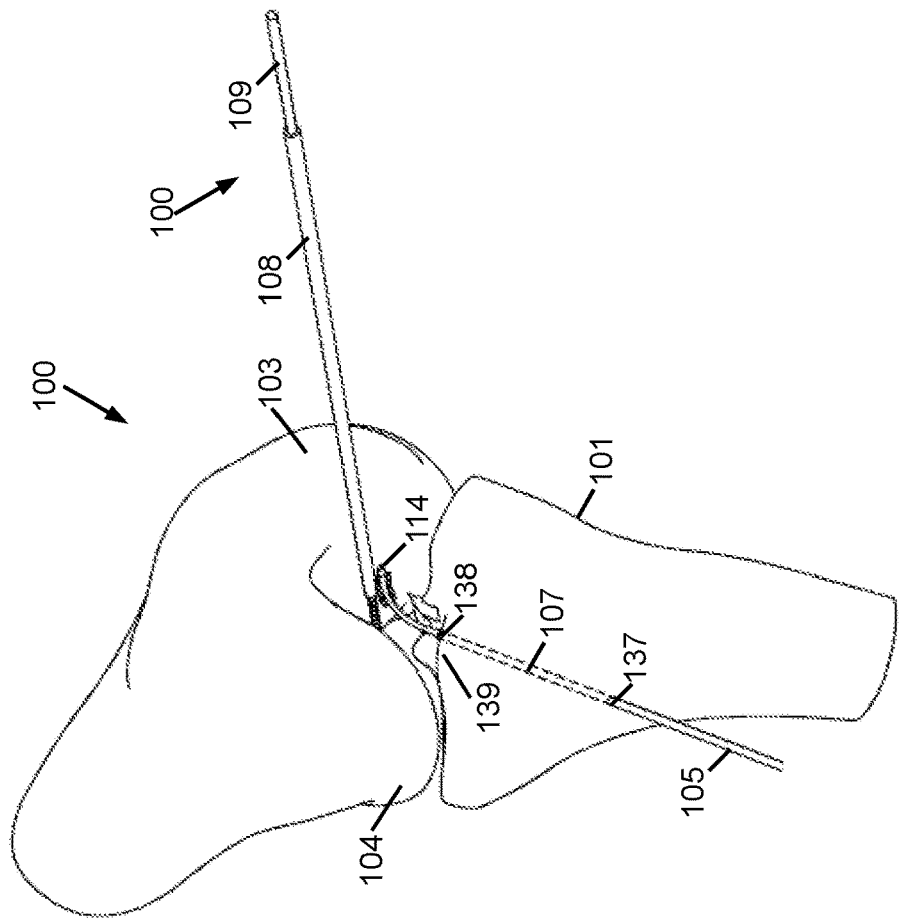

Referencing FIG. 2, the tip 106 of the guidewire 105 extending from a tibial plateau exit 138 is then bent between the femoral condyles 103, 104 towards a lateral condyle 103 ACL insertion point 114. There is typically 3-4 cm between the tibial and femoral surfaces within the joint 100.

FIG. 2 illustrates the utilisation of an optional guide 110 inserted through a medial portal for guiding the distal end of the guidewire 105 towards the ACL insertion point 114. FIG. 2B shows that the guide 110 may comprise a rod 108 and a distal guide wire engagement 111 which engages the guidewire 105 to bend the tip 106 of the guidewire 105 towards the ACL insertion point 114.

In the embodiment shown, the guide wire engagement 111 forms as an open channel which may have a curvature therealong which is transverse the elongate axis of the rod 108. As such, twisting of the rod 108 may correspondingly bend the distal end of the guidewire 105 towards the ACL insertion point 114.

In embodiments, the guide 110 may reference the femoral intercondylar notch (i.e. back of knee) to correctly position the guide wire anteroposteriorly. In accordance with this embodiment, the rod 108 may be cylindrical and the guide 111 may comprise an inner rod 109 slidably located therein. The guide wire engagement 111 may connect to the outer cylindrical section 108 such that the engagement 111 may be positioned with reference to the femoral intercondylar notch by adjusting the position of the rod 109 with respect to the outer cylindrical rod 108. The distal end of the inner rod 109 may comprise a step or other profile (not shown) shaped to conform and reference the notch. In embodiments the rod 109 may comprise depth gauge markings 112 either at the distal end thereof as shown or at the proximal end thereof for engaging the offset of the inner rod 109 with respect to the outer rod 100A to correctly position the tip 106 of the guidewire 105 anteroposteriorly.

FIG. 2B shows the distal portion of the guidewire 107 comprising a narrowing midsection 113 in embodiments allowing for greater flexibility to transition the bend within the joint 100 yet while having larger normal diameter sections at either end thereof to confer structural resilience at the cutting tip 107 and the proximal shaft of the guidewire 105. For example, the guidewire 105 may comprise a nominal diameter of 1.5 mm and the narrowing midsection 103 may comprise a length of approximately 1-2 cm and narrow down towards approximately 1.1 mm in diameter according to an hourglass-type profile. The engagement 111 may support the guidewire 105 at the relatively weaker narrowing midsection 113.

FIG. 3A illustrates the further drilling of the guidewire 105 to form a straight femoral passage 115 through the lateral condyle 103 from the ACL insertion point 114 to a superior posterolateral exit 140 such that the tip 106 extends from the femur 102. As can be seen, the femoral passage 115 is angled with respect to the tibial passage 107.

FIG. 3B illustrates the optional insertion of the distal end of the guidewire 105 into a depth gauge 116 having depth gauge markings 117 thereon so as to gauge the insertion depth of the guidewire 105, which may allow for subsequent gauging of the insertion depth of a reamer described below. In alternative embodiments, the depth gauge 116 may be used to gauge the depth of the reamer described below extending from the exit 140.

Figure 5A:
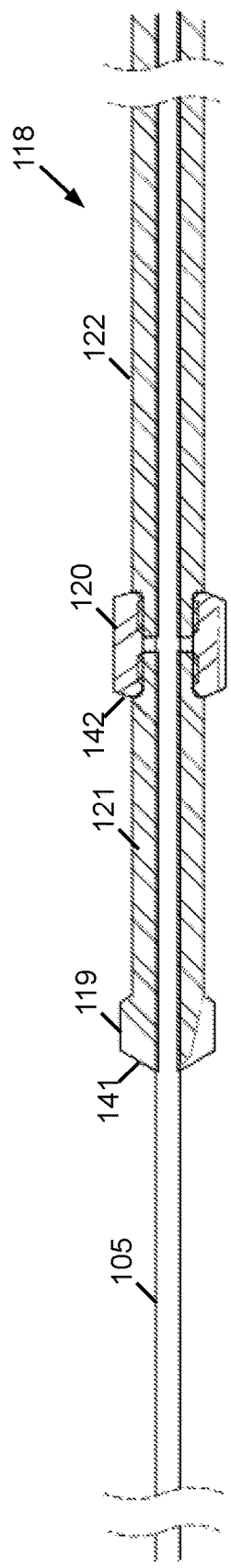
FIG. 5 illustrates cross-sectional views of a flexible reamer having cannulated and non-cannulated embodiments.
Figure 5B:
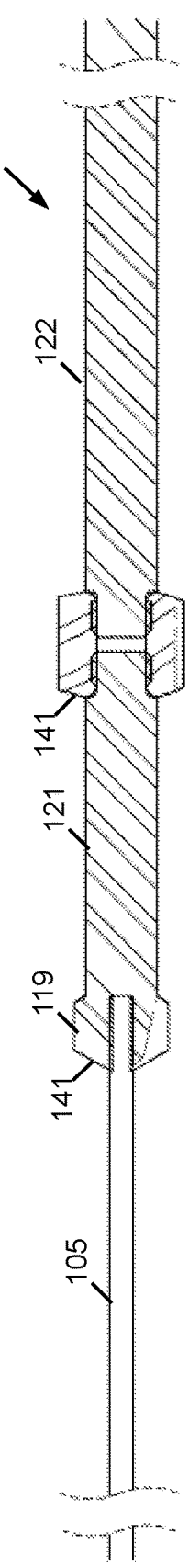

FIG. 5 shows an elongate reamer 118 comprising a distal cutting head 119 and a proximal cutting head 120. The proximal rotation cutting head 120 has a diameter greater than that of the distal cutting head 119. The reamer 118 further comprises a distal flexible shaft 121 coaxially connecting between the distal cutting head 119 and the proximal cutting head 120. The reamer may further comprise a proximal flexible shaft 122 connecting the proximal cutting head 120 proximally.

Figure 5C:
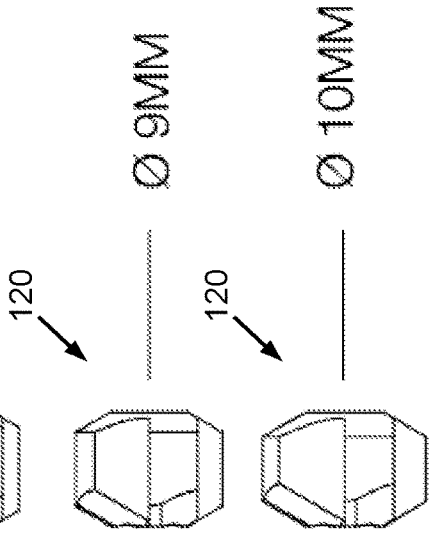

FIG. 5C shows a set of proximal cutting heads 120 of differing diameters that may be interchanged to suit differing patient anatomy in embodiments. In the embodiment shown, the proximal cutting head 120 may comprise diameters between 6 and 12 mms in 0.5 mm increments in accordance with an embodiment. The diameter of the distal cutting head 119 may be invariant, and less than 6 mm or 7 mm, typically between 4.5-5.5 mm The cutting heads 119, 120 define distal cutting faces 141, 142 for forward cutting. The distal cutting face 141 increases a passage diameter from that of the guidewire 105 to that of the distal cutting head 119 and distal cutting face 142 further increases the passage diameter from that of the distal cutting head 119 to that of the proximal cutting head 120.

The distal cutting faces 141, 142 may be symmetric along an elongate axis of the reamer so as to reduce or eliminate non-coaxial eccentricity when drilling.

Furthermore, the distal cutting faces 141, 142 may be rearwardly swept along the elongate axis of the reamer 118 such that the cutting radius thereof increases from a relatively smaller diameter to a relatively larger diameter as the reamer 118 is drilled forwardly, thereby enhancing coaxial alignment during reaming. For example, the rearward angle of the distal cutting head 119 defines a distal end having a relatively narrower diameter that matches the diameter of the guidewire 105 to coaxially follow at the perimeter of the passage formed by the guidewire 105 and which enlarges proximally to the relatively larger proximal maximum diameter of the angled distal cutting face 141. In embodiment shown, the cutting faces 141, 142 may be substantially frustoconical or cut frustoconically.

In embodiments, the cutting heads 119, 120 may define proximal rearward rounded faces for easier rearward pulling of the reamer 118 from the joint 100.

The elongate distal flexible shaft 121 may be flexible by virtue of differing mechanical arrangements within the purposive scope of the embodiments described herein. For example, the elongate distal flexible shaft 121 may comprise a spiral formation, constituent interlocking pieces and the like conferring flexibility to the portion 121. In embodiments, the portion 121 may even be integrally formed from sufficiently resilient yet bendable plastic, metal or rubber tubing.

The elongate reamer 118 is configured for coaxially engaging the guidewire 105 from the distal cutting head 119.

FIG. 5A illustrates a cannulated version of the reamer 118 wherein the reamer 118 is entirely cannulated therealong so as to allow the cutting heads 119, 120 to follow in-line over the guidewire 105. As such, during reaming, the cutting heads 119, 120 move relative to the guidewire 105 along the inner get axis of the reamer 118.

However, in a preferred embodiment, the reamer 118 is connected to the guidewire 105 such that the guidewire 105 and the reamer 118 move together through the joint along the elongate axis of the reamer.

By not being entirely cannulated in this embodiment, friction between the reamer 118 and the guidewire 105 and potential for metallosis or breakage can be eliminated or reduced.

Furthermore, should the reamer 118 break in two during operation, the distal portion may yet remain connected to the guidewire 105 for retrieval.

In embodiments the guidewire 105 may be connected to the reamer 118 such that the reamer 118 is able to rotate with respect to the guidewire 105 but that the guidewire 105 and the reamer 118 cannot move relatively along the elongate axis of the reamer 118. In accordance with this embodiment, the guidewire 105 may connect to the reamer 118 by way of a rotational bearing.

In one embodiment, the distal cutting head 119 may define a central port having an inner annular recess within which a detent at a proximal end of the guidewire 105 interferes. As such, the proximal end of the guidewire 105 may be pushed into a distal opening of the distal cutting head 119 causing the detent to be depressed until such time that the detent extends at the inner annular recess so as to rotatably engage the distal cutting head 119 yet while being able to apply traction thereto.

However, in a further preferred embodiment, the guidewire 105 and the reamer 118 are connected such that the guidewire 105 and the reamer 118 rotate together thereby eliminating friction between the guidewire 105 and the distal cutting head 115 and further allowing for an enhanced mechanical coupling therebetween. In one embodiment, the proximal end of the guidewire 105 may comprise threading which screws into complimentary threading of a distal port of the distal cutting head 119. The threading may be configured to tighten in the same direction of rotation of the reamer 118. Other mechanical interlock may be employed also, including keyed interlocks which insert at one angle and lock at a rotationally offset angle.

Whereas the reamer 118 may be integrally constructed, FIG. 4A shows a reamer of modular construction which allows for the interchange of components, including the proximal cutting head 120 in accordance with patient specific anatomy. FIG. 4A shows the distal cutting head 119 and the distal flexible shaft 121 being integrally constructed and separable from the proximal cutting head 120 which is itself separable from the proximal flexible shaft 122. This particular configuration allows for the interchange of the proximal cutting head 120 to suit patient specific anatomy as alluded to above.

In embodiments, these components may screw together wherein, in embodiments, complimentary threading thereof may tighten in the same direction of rotation of the reamer during drilling so as to avoid inadvertent unscrewing during reaming. Other embodiments may have the proximal and distal cutting heads integrally connected by a flexible segment as one piece.

In embodiments, the proximal end of the guidewire 105 may comprise a small aperture 123 for retaining a suture therethrough.

FIG. 4B shows attaching the reamer 118 to the proximal end of the guidewire 105 located within the joint 100.

Figure 6:
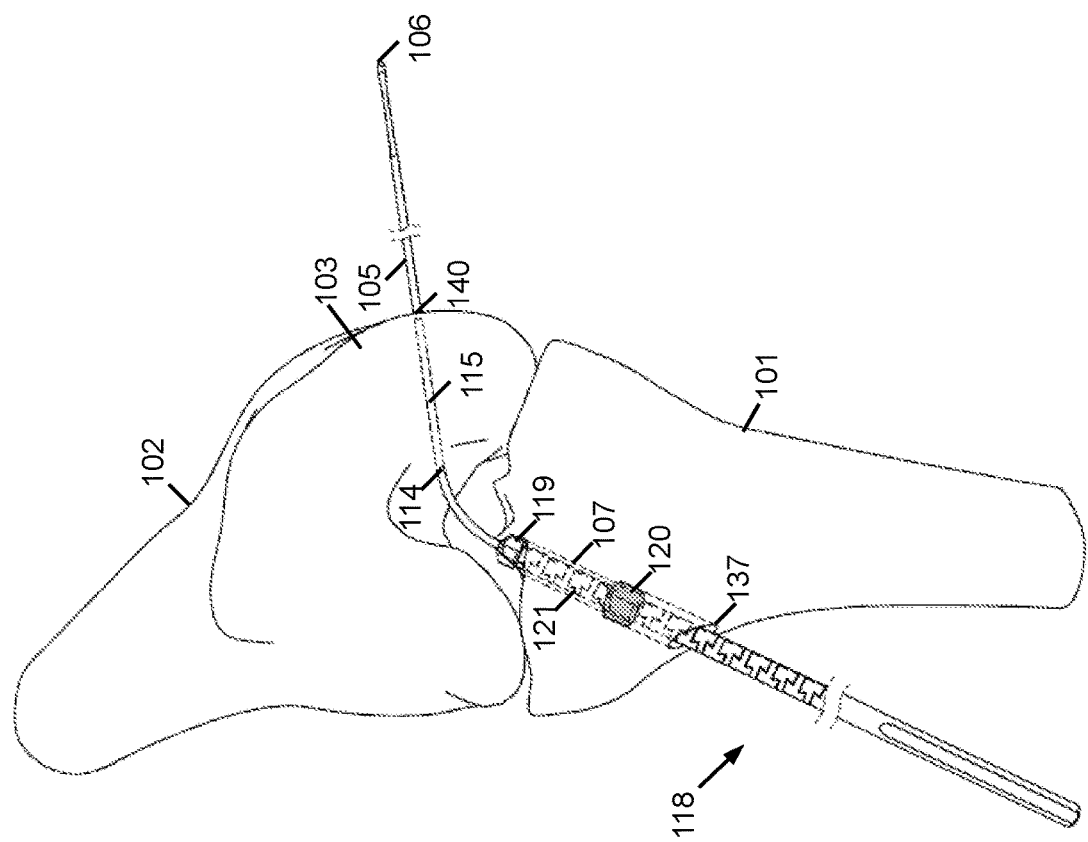
FIGS. 6-8 illustrate the following of the guidewire by the flexible reamer through the tibial passage and out from the femoral passage.

FIG. 6 shows the reamer 118 being drilled to follow the guidewire 105 straight through the tibial passage, thereby widening the tibial passage 107 to the diameter of the proximal cutting head 120. As can be seen, the reamer 118 drills straight through the tibial passage 107.

Figure 7:
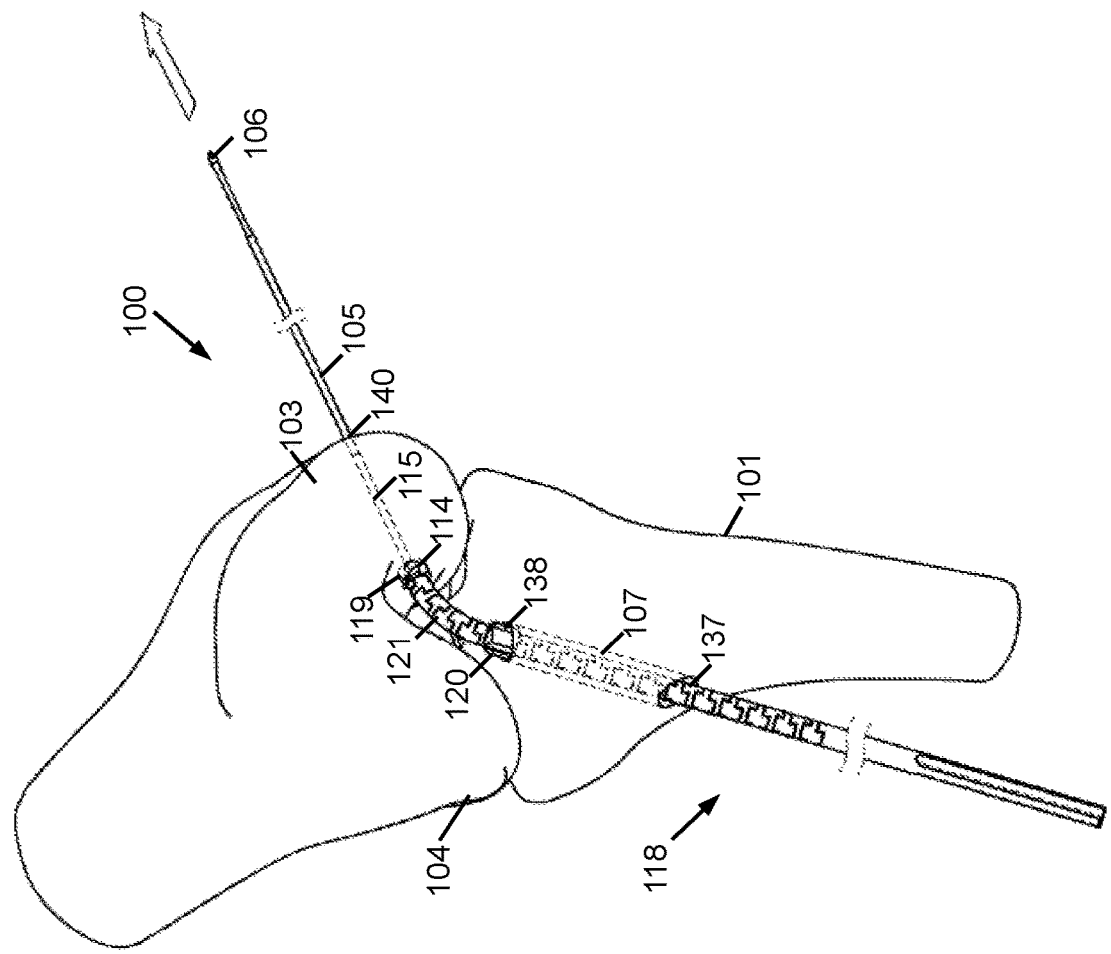

FIG. 7 shows the reamer 118 following the guidewire 105 to bend within the joint 100 between the tibial plateau exit 138 and the ACL insertion point 114.

Figure 8:
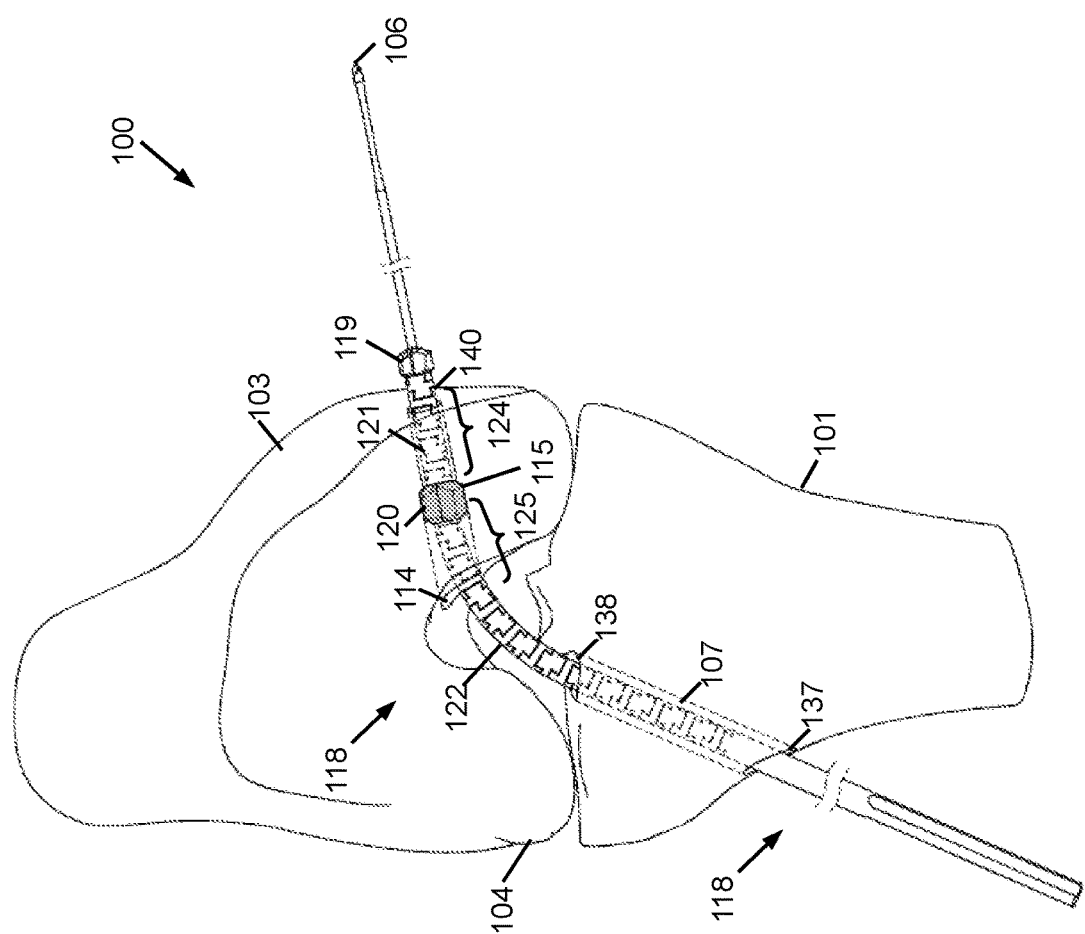

FIG. 8 shows the reamer 118 having drilled straight through the femoral passage 115 until the distal cutting head 119 passes through the superior posterior lateral exit 140 and the proximal cutting head 120 locates between the ACL insertion point 114 and the superior posterior lateral exit 140. At this location, the reamer 118 has enlarged the femoral passage 115 to comprise a medial passage portion 125 having the diameter of the proximal cutting head 120 and a lateral passage portion 124 having a diameter of the proximal cutting head 119.

In embodiments, the guidewire 105 may be pulled to assist the reamer 118 through the joint 100. In embodiments, a distal end of the guidewire 105 may comprise a peripheral recess for rotatably engaging collar of the tool for pulling the guidewire 105 either while the guidewire 105 rotates with the reamer 118 or remains relatively static.

Figure 9:
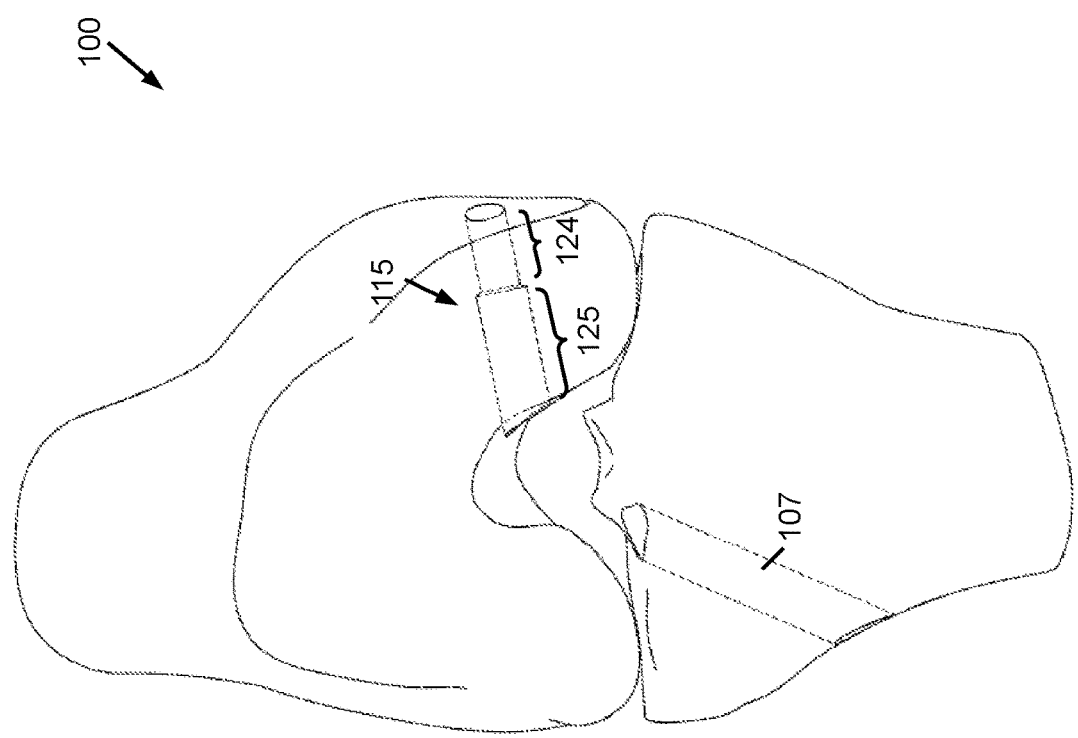
FIG. 9 illustrates the tibial and femoral passages formed by the flexible reamer, including the femoral passage comprising the lateral smaller diameter section and the medial larger diameter section.

FIG. 9 shows the reamer 118 having being pulled by the proximal end thereof from the knee joint 100 having widened the tibial passage 107 and the medial passage portion 125 to the diameter of the proximal cutting head 120 and the lateral passage portion 124 to the diameter of the distal cutting head 119.

An anterior cruciate ligament replacement can then be inserted and secured within the formed tibial and femoral passages 107, 115, including by endobutton fixation technique.

Figure 10B:
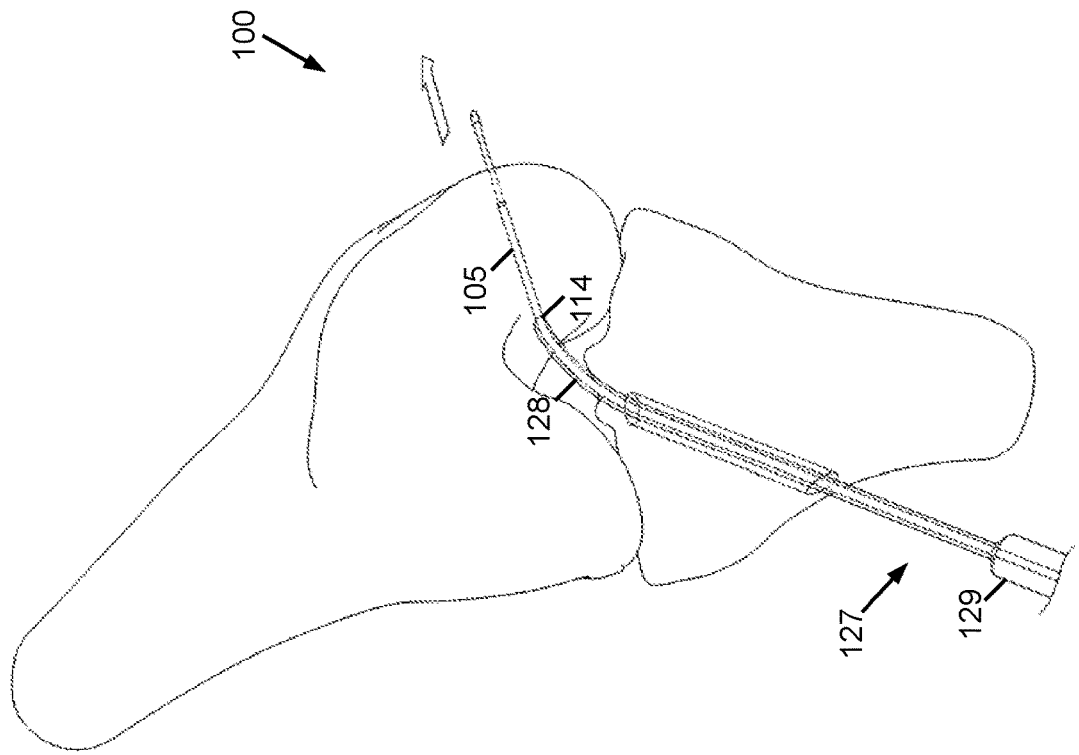
FIG. 10 illustrates the utilisation of curved insertion guide inserted through a larger diameter tibial passage to guide the guidewire towards the appropriate ACL insertion point.
Figure 10A:
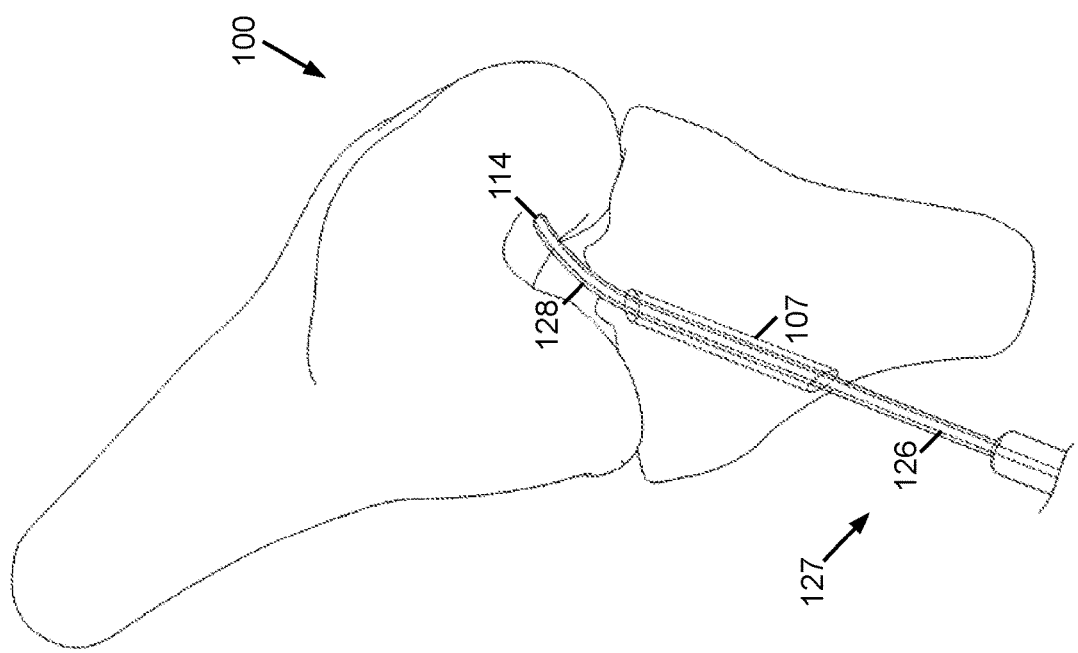

FIG. 10 shows an embodiment involving the utilisation of a cannulated guide 127. The cannulated guide 127 may comprise a proximal straight section 126 and a distal curved section 128.

Utilisation of the cannulated guide 127 comprises formation of the tibial passage 107 with a sufficiently large diameter to allow the straight insertion of the curved section 128 therethrough. Once the curved section 128 locates within the joint, the distal end thereof is able to find the ACL insertion point so as to be able to guide the guidewire therethrough. When locating ACL insertion point 114, a side of the straight section 126 may be pressed against a side of the tibial passage 107 to reference the location of the distal end of the curved section 128

The curved section 128 may be angled to find the ACL insertion point 114 when inserted in the manner shown. The rotational orientation of the cannulated guide 127 may be referenced with an anatomically referencing dial 129 at a posterior end thereof.

Figure 11B:
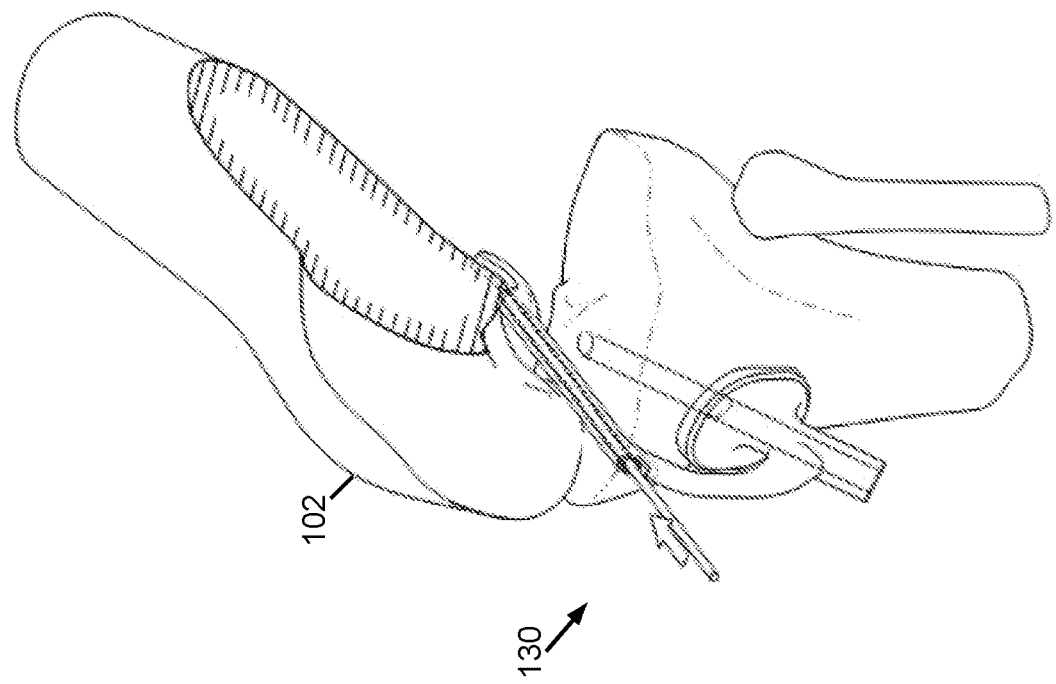
FIG. 11 illustrates a custom guide for marking the appropriate ACL insertion point in accordance with an embodiment.
Figure 11B:
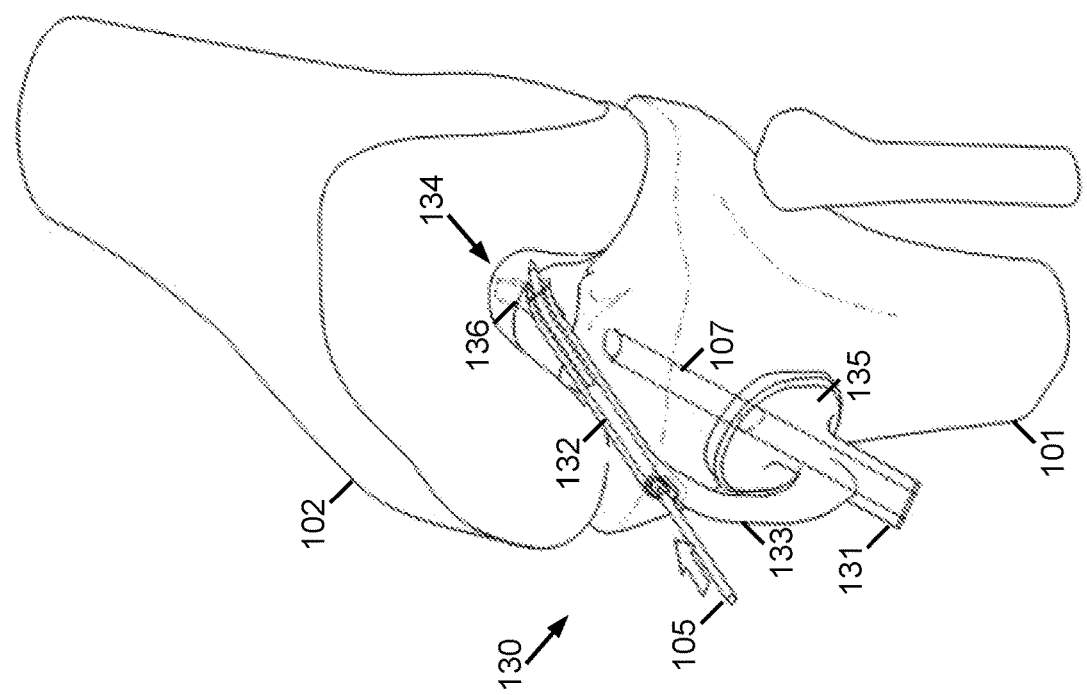

FIG. 11 illustrates the utilisation of a custom guide 130. The custom guide 130 comprises a tibial guide passage 131 and a femoral guide passage 132 which are joined at an angle by an arm 133 therebetween.

The tibial guide passage 131 may meet a plate 135 which references the anteromedial aspect of the tibia 101. Furthermore, a distal end of the femoral guide passage 132 may comprise a step 134 which references the femoral intercondylar notch.

As such, the custom guide 130 is able to accurately fixation at two points between the fixed anteromedial aspect of the tibia 101 and the intercondylar notch of the femur 136.

In embodiments, the custom guide 130 may further locate at a third point wherein an inferior protrusion (not shown) extends downwardly from the femoral guide passage 132 to contact an upper surface of the tibia 101 in the joint, such as the distal exit of the tibial passage 107.

In a preferred embodiment, the custom guide 130 is custom manufactured according to patient specific anatomy which may be derived from preoperative imaging such as x-ray, CT MRI imaging or the like. Specifically, a computer model of the joint 100 may be generated from such imaging and the ACL insertion point 114 placed thereon and the tibial insertion entrance of the ACL similarly found for the patient's specific anatomy. Thereafter, the custom guide 130 may be configured such that, when 3D printed, locates the guidewire at the chosen ACL insertion point 114 and the tibial insertion entrance.

The utilisation of the custom guide 130 comprises driving a guide wire through tibial passage guide 131 and then reaming over the guide wire to form the tibial passage 107 replicating centre of tibial insertion entrance in the knee joint Furthermore, the guidewire 105 may be inserted through the femoral guide passage 132 so as to contact the inner surface of the femur at the appropriate ACL insertion point 114. The distal end of the guidewire 105 may be used to mark the reference point 114 whereafter the guidewire 105 and the custom guide 130 may be withdrawn and the femoral passage 115 reamed in chosen manner with reference to the marking.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method of anterior cruciate ligament reconstruction for a knee joint comprising a tibia and a femur, the method comprising: drilling a guide wire to form a straight tibial passage through the tibia between an inferior anteromedial entrance and a tibial plateau exit of the tibia; bending a tip of the guide wire extending from a tibial plateau exit towards an ACL insertion point at a lateral condyle of the femur; further drilling the guide wire to further form a straight femoral passage through the lateral condyle between the ACL insertion point and a superior posterolateral exit such that the tip extends from the femur and the femoral passage is angled with respect to the tibial passage; attaching a reamer to a proximal end of the guidewire, the reamer comprising a distal cutting head, a distal flexible shaft, a proximal cutting head and a proximal flexible shaft and wherein the proximal cutting head has a greater cutting diameter than that of the distal cutting head; drilling the reamer to follow the guidewire such that the reamer follows the guidewire straight through the tibial passage, bends between the tibial plateau exit and the ACL insertion point and follows straight through the femoral passage until the distal cutting head passes through the superior posterolateral exit and the proximal cutting head locates between the ACL insertion point and the superior posterolateral exit; pulling the proximal end of the reamer to pull the reamer from the knee joint, thereby having enlarged the tibial passage to the diameter of the proximal cutting head and having enlarged the femoral passage to comprise a medial passage portion having the diameter of the proximal cutting head and a lateral passage portion having a diameter of the distal cutting head; and inserting and securing an anterior cruciate ligament replacement within the tibial passage and the femoral passage.

2. The method as claimed in claim 1, wherein a proximal end of the guide wire is connected to the distal cutting head such that the guide wire and the proximal cutting head move in alignment together along an elongate axis of the reamer during reaming.

3. The method as claimed in claim 2, wherein the method further comprises pulling the distal end of the guidewire during reaming to pull the reamer through the knee joint.

4. The method as claimed in claim 2, wherein the proximal end of the guide wire is connected to a distal side of the distal cutting head such that the guide wire and the proximal cutting head rotate together.

5. The method as claimed in claim 4, wherein the proximal end of the guidewire comprises threading which screws into threading of a central port of the distal cutting head.

6. The method as claimed in claim 5, wherein the threading is respectively orientated to tighten when the reamer rotates during reaming.

7. The method as claimed in claim 1, wherein the distal cutting head defines a distal cutting face and wherein the distal cutting face is rearwardly swept.

8. The method as claimed in claim 7, wherein the distal cutting face cuts frustoconically.

9. The method as claimed in claim 1, wherein the method further comprises referencing the insertion depth of the proximal cutting head by referencing the length of the distal flexible shaft extending from the superior posterolateral exit.

10. The method as claimed in claim 1, wherein the method further comprises using an elongate reference guide having depth reference markings thereon by placing the elongate reference guide against the lateral condyle the superior posterolateral exit and reading the location of the distal flexible shaft with reference to the depth reference markings.

11. The method as claimed in claim 1, wherein the method comprises interchanging the proximal cutting head with another cutting head of a specific diameter according to patient specific anatomy.

12. The method as claimed in claim 1, wherein the reamer is a modular reamer of modular construction such that at least the proximal cutting head is separable.

13. The method as claimed in claim 12, wherein the modular reamer has the distal cutting head and the distal flexible shaft being inseparable.

14. The method as claimed in claim 12, wherein a proximal end of the distal flexible shaft comprises threading which screws into threading of a central port of the proximal cutting head.

15. The method as claimed in claim 14, wherein the threading is respectively orientated to tighten when the reamer rotates during reaming.

16. The method as claimed in claim 1, further comprising inserting a bending guide between the femoral condyles to bend the tip of the guidewire towards the ACL insertion point.

17. The method as claimed in claim 16, wherein the bending guide comprises a rod and a guide wire engagement transversely orientated at a distal end thereof.

18. The method as claimed in claim 17, wherein the guide wire engagement defines a transverse open channel which engages the guidewire there along.

19. The method as claimed in claim 18, wherein the transverse open channel is curved.

20. The method as claimed in claim 17, wherein the rod is cylindrical and wherein the bending guide further comprises an inner rod which references a point of the knee joint and wherein the method further comprises positioning the anteroposterior location of the tip of the guidewire by gauging the offset of the rod and the inner rod.

21. The method as claimed in claim 20, wherein the inner rod has depth gauge markings thereon.

22. The method as claimed in claim 16, wherein inserting the bending guide comprises inserting the bending guide through an incision.

23. The method as claimed in claim 1, wherein the distal cutting head comprises a diameter of less than 7 mm.

24. The method as claimed in claim 1, wherein the distal cutting head comprises a diameter of less than 6 mm.

25. The method as claimed in claim 1, wherein the proximal cutting head comprises a diameter of greater than 6 mm.

\* \* \* \* \*